United States Patent [19]

Powell et al.

[11] Patent Number: 5,777,182

[45] Date of Patent: *Jul. 7, 1998

[54] COBALT-CATALYZED PROCESS FOR PREPARING 1,3-PROPANDIOL

[75] Inventors: Joseph Broun Powell; Lynn Henry Slaugh, both of Houston; Thomas Clayton Forschner, Richmond; Jiang-Jen Lin, Houston; Terry Blane Thomason, Houston; Paul Richard Weider, Houston; Thomas Carl Semple, Friendswood; Juan Pedro Arhancet, Katy; Howard Lam-Ho Fong, Sugar Land; Stephen Blake Mullin; Kevin Dale Allen, both of Katy; David Cleve Eubanks, Houston; David William Johnson, Richmond, all of Tex.

[73] Assignee: Shell Oil Company, Houston, Tex.

[*] Notice: The term of this patent shall not extend beyond the expiration date of Pat. No. 5,463,145.

[21] Appl. No.: 703,295

[22] Filed: Aug. 26, 1996

Related U.S. Application Data

[63] Continuation-in-part of Ser. No. 316,676, Sep. 30, 1994, and a continuation-in-part of Ser. No. 316,660, Sep. 30, 1994, Pat. No. 5,585,528, and a continuation-in-part of Ser. No. 316,669, Sep. 30, 1994, Pat. No. 5,576,471, and a continuation-in-part of Ser. No. 316,680, Sep. 30, 1994, Pat. No. 5,563,302.

[51] Int. Cl.$^6$ ................................. C07C 27/04
[52] U.S. Cl. .................. 568/862; 568/454; 568/483
[58] Field of Search ..................... 568/454, 483, 568/862

[56] References Cited

U.S. PATENT DOCUMENTS

| | | | |
|---|---|---|---|
| 3,021,314 | 2/1962 | Cox et al. | 260/78.3 |
| 3,021,316 | 2/1962 | Cox et al. | 260/78.3 |
| 3,063,967 | 11/1962 | Schultz | 260/78.3 |
| 3,063,968 | 11/1962 | Schultz | 260/78.3 |
| 3,168,553 | 2/1965 | Slaugh | 260/497 |
| 3,391,126 | 7/1968 | Baggett et al. | 260/78.3 |
| 3,456,017 | 7/1969 | Smith et al. | 260/602 |
| 3,463,819 | 8/1969 | Smith et al. | 260/602 |
| 3,645,941 | 2/1972 | Snapp et al. | 260/18 |
| 3,687,981 | 8/1972 | Lawrence et al. | 260/340.7 |
| 4,137,240 | 1/1979 | Peterson | 260/340.7 |
| 4,255,279 | 3/1981 | Spohn et al. | 252/413 |
| 4,404,119 | 9/1983 | Lagace et al. | 252/413 |
| 4,653,497 | 3/1987 | Bezwada et al. | 128/335.6 |
| 4,873,378 | 10/1989 | Murphy et al. | 568/867 |
| 4,873,379 | 10/1989 | Murphy | 568/867 |
| 4,973,741 | 11/1990 | Beavers | 569/428 |
| 5,030,766 | 7/1991 | Briggs et al. | 568/496 |
| 5,047,048 | 9/1991 | Bezwada et al. | 606/231 |
| 5,053,562 | 10/1991 | Tau | 568/867 |
| 5,210,318 | 5/1993 | Briggs | 568/496 |
| 5,225,387 | 7/1993 | Briggs et al. | 502/167 |
| 5,256,827 | 10/1993 | Slaugh | 568/454 |
| 5,310,945 | 5/1994 | Forschner | 549/274 |
| 5,321,168 | 6/1994 | Roussel et al. | 568/882 |
| 5,504,261 | 4/1996 | Mullin et al. | 568/862 |

OTHER PUBLICATIONS

Falbe, Carbon Monoxide In Organic Synthesis, Springer-Verlag (1970), pp. 14–15.
Falbe, New Synthesis With Carbon Monoxide, Springer-Verlag (1980), p. 131.

*Primary Examiner*—Rebecca Cook

[57] ABSTRACT

1,3-propanediol is prepared in a process which involves hydroformylating ethylene oxide:

(a) in an essentially non-water-miscible solvent in the presence of a non-ligated cobalt catalyst and a catalyst promoter at a temperature within the range of about 50° to about 100° C. and a pressure within the range of about 500 to about 5000 psig, to produce an intermediate product mixture comprising less than about 15 wt % 3-hydroxypropanal;

(b) adding an aqueous liquid and extracting at a temperature less than about 100° C. the 3-hydroxypropanal to provide an aqueous phase comprising 3-hydroxypropanal in greater concentration than the concentration of 3-hydroxypropanal in said intermediate product mixture, and an organic phase comprising the cobalt catalyst;

(c) separating the aqueous phase from the organic phase;

(d) hydrogenating the 3-hydroxypropanal to provide a hydrogenation product mixture comprising 1,3-propanediol; and (e) recovering 1,3-propanediol from said hydrogenation product mixture.

The process enables the production of 1,3-propanediol in high yields and selectivity without the use of a phosphine ligand-modified cobalt catalyst.

18 Claims, 1 Drawing Sheet

COBALT-CATALYZED PROCESS FOR PREPARING 1,3-PROPANIDIOL

CROSS-REFERENCES TO RELATED APPLICATIONS

This application is a continuation-in-part of Ser. No. 316,676 abandoned; Ser. No. 316,660 now U.S. Pat. No. 5,585,528; Ser. No. 316,669 now U.S. Pat. No. 5,576,471; and Ser. No. 316,680, now U.S. Pat No. 5,563,302, all filed Sep. 30, 1994.

BACKGROUND OF THE INVENTION

This invention relates to the preparation of 1,3-propanediol. In one aspect, the invention relates to a cobalt-catalyzed process for manufacturing 1,3-propanediol in high yields without the use of a phosphine ligand for the cobalt catalyst.

1,3-propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) hydrogenation of the HPA to PDO. The initial hydroformylation step can be carried out at temperatures greater than 100° C. and at high syngas pressures to achieve practical reaction rates. The resulting product mixture is, however, rather unselective for HPA.

In an alternate hydroformylation method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare HPA in a low temperature, selective process which did not require the use of a phosphine ligand with the cobalt catalyst.

It is therefore an object of the invention to provide an economical process for the preparation of 1,3-propanediol which does not require the use of a phosphine-ligated catalyst for preparation of the HPA intermediate.

SUMMARY OF THE INVENTION

According to the invention, 1,3-propanediol is prepared in a process comprising the steps of:

(a) contacting ethylene oxide with carbon monoxide and hydrogen in an essentially non-water-miscible solvent in the presence of an effective amount of a non-phosphine-ligated cobalt catalyst and an effective amount of a catalyst promoter at a temperature within the range of about 50° to about 100° C. and a pressure within the range of about 500 to about 5000 psig, under reaction conditions effective to produce an intermediate product mixture comprising less than about 15 wt % 3-hydroxypropanal;

(b) adding an aqueous liquid to said intermediate product mixture and extracting into said aqueous liquid at a temperature less than about 100° C. a major portion of the 3-hydroxypropanal to provide an aqueous phase comprising 3-hydroxypropanal in greater concentration than the concentration of 3-hydroxypropanal in said intermediate product mixture, and an organic phase comprising at least a portion of the cobalt catalyst or a cobalt-containing derivative thereof;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least 40° C. to provide a hydrogenation product mixture comprising 1,3-propanediol; and (e) recovering 1,3-propanediol from said hydrogenation product mixture.

The process enables the production of 1,3-propanediol in high yields and selectivity without the use of a phosphine-ligated cobalt catalyst in the hydroformylation step.

DETAILED DESCRIPTION OF THE INVENTION

Figure 1:
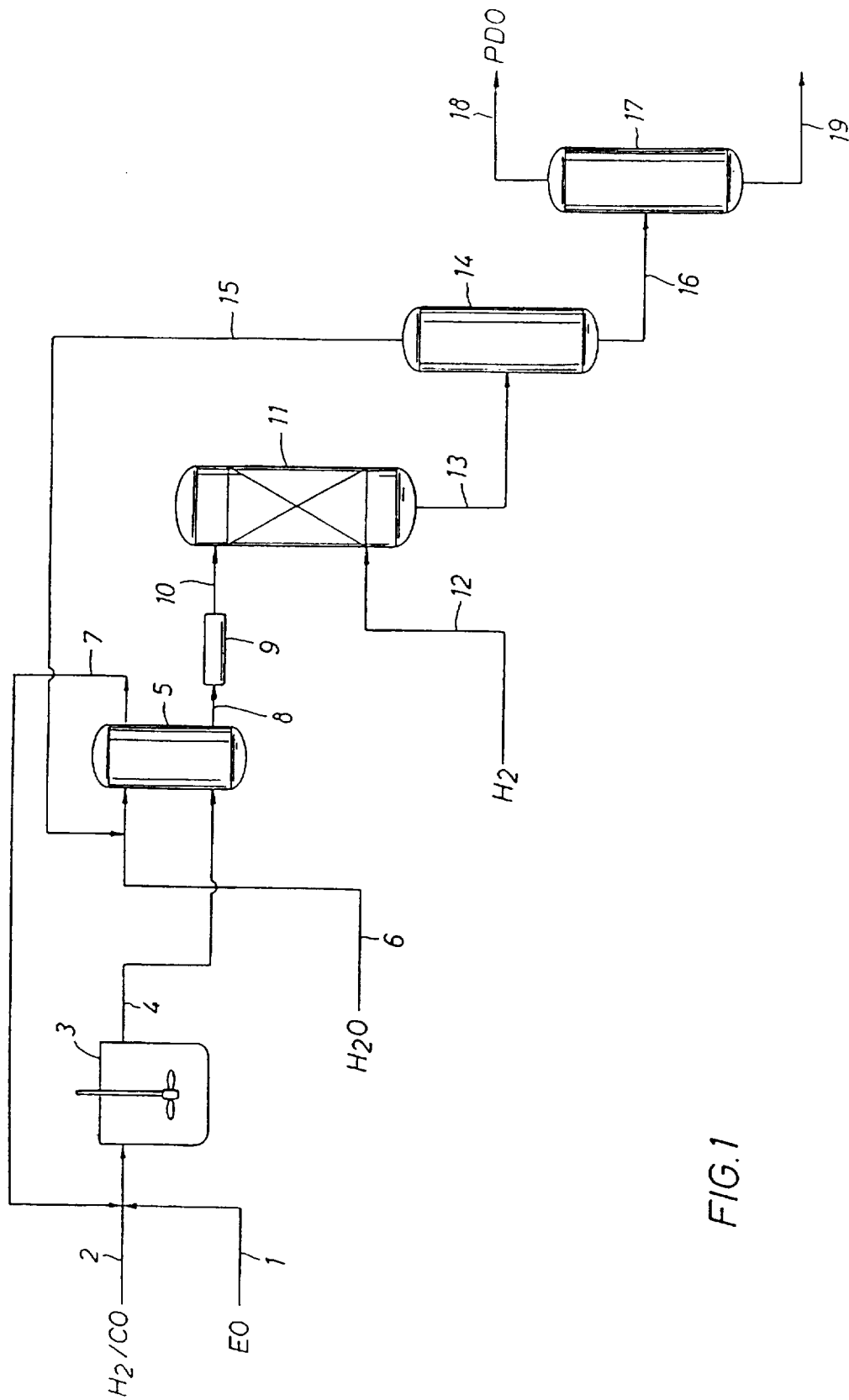
FIG. 1 is a schematic flow diagram of one embodiment of the invention 1,3-propanediol preparation process.

The invention 1,3-propanediol preparation process can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt catalyst, i.e., a cobalt carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction product mixture containing a major portion of 3-hydroxypropanal (HPA) and a minor portion of acetaldehyde, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.) Generally, the hydroformylation reaction is carried out at elevated temperature less than 100° C., preferably about 60° to about 90° C., most preferably about 75° to about 85° C., and at a pressure within the range of about 500 to about 5000 psig, preferably (for process economics) about 1000 to about 3500 psig, with higher pressures preferred for greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C.) and relatively short residence times (about 20 minutes to about 1 hour) are preferred. In the practice of the invention method, it is possible to achieve HPA yields (based on ethylene oxide conversion) of greater than 80%, with formation of greater than 7 wt % HPA, at rates greater than 30 $h^{-1}$. (Catalytic rates are referred to herein in terms of "turnover frequency" or "TOF" and are expressed in units of moles per mole of cobalt per hour, or $h^{-1}$.) Reported rates are based on the observation that, before a majority of EO is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula

$$R_2\text{—}O\text{—}R_1 \quad (1)$$

in which $R_1$ is hydrogen or $C_{1-20}$ linear, branched, cyclic or aromatic hydrocarbyl or mono- or polyalkylene oxide and $R_2$ is $C_{1-20}$ linear, branched, cyclic or aromatic hydrocarbyl, alkoxy or mono- or polyalkylene oxide. The most preferred hydroformylation solvents can be described by the formula

$$\begin{array}{c} R_3 \\ | \\ R_4\text{—}C\text{—}O\text{—}R_1 \\ | \\ R_5 \end{array} \quad (2)$$

in which $R_1$ is hydrogen or $C_{1-8}$ hydrocarbyl and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. Although phosphine-ligated catalysts are active for hydroformylation reactions, the invention process is designed to achieve good yield and selectivity without the additional expense of the ligand. The cobalt catalyst can be supplied to the hydroformylation reactor in essentially any form including metal, supported metal, Raney-cobalt, hydroxide, oxide, carbonate, sulfate, acetylacetonate, salt of a carboxylic acid, or as an aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed in situ via reaction with $H_2$ and Co, as described in J. Falbe, "Carbon Monoxide in Organic Synthesis," Springer-Verlag, NY (1970). In general, catalyst formation conditions will include a temperature of at least 50° C. and a carbon monoxide partial pressure of at least about 100 psig. For more rapid reaction, temperatures of about 120° to 200° C. should be employed, at CO pressures of at least 500 psig. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the cobalt carbonyl under $H_2/CO$ from cobalt hydroxide in the presence of a small amount of seed cobalt carbonyl. The conversion of $Co^{2+}$ to the desired cobalt carbonyl is carried out at a temperature within the range of about 75° to about 200° C., preferably about 100° to about 140° C. and a pressure within the range of about 1000 to about 5000 psig for a time preferably less than about 3 hours. The preforming step can be carried out in a pressurized preforming reactor or in situ in the hydroformylation reactor.

The amount of cobalt present in the reaction mixture will vary depending upon the other reaction conditions, but will generally fall within the range of about 0.01 to about 1 wt %, preferably about 0.05 to about 0.3 wt %, based on the weight of the reaction mixture.

The hydroformylation reaction mixture will preferably include a catalyst promoter to accelerate the reaction rate. Suitable promoters include sources of mono- and multivalent metal cations of weak bases such as alkali, alkaline earth and rare earth metal salts of carboxylic acids. Also suitable are lipophilic promoters such as lipophilic phosphonium salts and lipophilic amines, which accelerate the rate of hydroformylation without imparting hydrophilicity (water solubility) to the active catalyst. As used herein, "lipophilic" means that the promoter tends to remain in the organic phase after extraction of HPA with water. The promoter will generally be present in an amount within the range of about 0.01 to about 0.6 moles per mole of cobalt. The currently preferred metal salt, because of its availability and demonstrated promotion of ethylene oxide hydroformylation, is sodium acetate. Suitable lipophilic promoters include tertiary amines such as nonylpyridine and dimethyldodecylamine; lipophilic phosphonium salts such as tetrabutylphosphonium acetate; lipophilic ammonium salts such as quaternary ammonium acetate; lipophilic phosphine oxides such as triphenylphosphine oxide; and lipophilic dihydroxyarenes such as hydroquinone. The currently preferred lipophilic promoters are dimethyldodecylamine, nonylpyridine and tetrabutylphosphonium acetate.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butylether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the cobalt catalyst and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO and recovery of PDO product. The water extraction is preferably carried out at a temperature within the range of about 25° to about 55° C., with higher temperatures avoided to minimize condensation products (heavy ends) and catalyst disproportionation to inactive, water-soluble cobalt species. In order to maximize catalyst recovery, it is optional but preferred to perform the water extraction under 50 to 200 psig carbon monoxide at 25° to 55° C.

The organic phase containing the reaction solvent and the major portion of the cobalt catalyst can be recycled from the extraction vessel to the hydroformylation reaction via 7. Aqueous extract 8 is optionally passed through one or more acid ion exchange resin beds 9 for removal of any cobalt catalyst present, and the decobalted aqueous product mixture 10 is passed to hydrogenation vessel 11 and reacted with hydrogen 12 in the presence of a hydrogenation catalyst to produce a hydrogenation product mixture 13 containing 1,3-propanediol. The hydrogenation step may also revert some heavy ends to PDO. The solvent and extractant water 15 can be recovered by distillation in column 14 and recycled to the water extraction process via a further distillation (not shown) for separation and purge of light ends. PDO-containing stream product 16 can be passed to distillation column 17 for recovery of PDO 18 from heavy ends 19.

Hydrogenation of the HPA to PDO can be carried out in aqueous solution at an elevated temperature during at least a portion of the hydrogenation step of about 40° C., generally within the range of about 50° to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures and alloys thereof. Fixed-bed nickel catalysts are currently preferred.

Commercial operation will require efficient cobalt catalyst recovery with essentially complete recycle of cobalt to the hydroformylation reaction. The preferred catalyst recovery process involves two steps, beginning with the above-described water extraction of HPA from the hydroformylation product mixture. A portion of the cobalt catalyst may remain in the organic phase, with the remaining cobalt catalyst passing into the water phase. The organic phase can be recycled to the hydroformylation reactor, with optional purge of heavy ends. Optionally, further decobalting of catalyst in the water layer can be effected by any suitable method, such as complete or partial oxidation of cobalt followed by precipitation and filtration, distillation, deposition on a solid support, or extraction using a suitable extractant, preferably prior to final cobalt removal by ion exchange (9).

The invention process permits the selective and economic synthesis of PDO at moderate temperatures and pressures without the use of a phosphine ligand for the hydroformylation catalyst. The process involves preparation of a reaction product mixture dilute in intermediate HPA, then concentration of this HPA by water extraction followed by hydrogenation of the aqueous HPA to PDO.

EXAMPLE 1

This comparison example illustrates the hydroformylation of ethylene oxide catalyzed by a phosphine-ligated cobalt catalyst derived from dicobaltoctacarbonyl.

A 300-ml stirred reactor was charged with 0.87 grams of dicobaltoctacarbonyl, 1.33 grams of bis(1,2-diphenylphosphino)ethane, 0.125 grams of sodium acetate trihydrate, 0.51 grams 2-ethylhexanoic acid, and 147.2 grams of Neodol® 23, a blend of $C_{12}$ and $C_{13}$ alcohols. Reactor contents were heated to 165° C. under 1:1 $H_2$:CO ("syngas") for 1 hour, with agitation at 1000 rpm, to preform the active catalyst. The reactor temperature was decreased to 90° C., and 20 grams of ethylene oxide were injected via a "blowcase" vessel charged with 1500 psig syngas. The reactor pressure was topped to 1500 psig. Reactor pressure decreased over time as a result of hydroformylation of EO substrate. The reactor was refilled to 1500 psig with 1:1 $H_2$:CO upon a decrease in pressure to about 1300 psig. In this manner, the uptake of synthesis gas could be monitored as a function of time, to follow the course of the reaction.

Samples of the reaction mixture were periodically withdrawn into chilled n-propanol containing an internal standard (toluene or ethylacetate) for analysis by capillary gas chromatography. The analysis indicated an 87% conversion of EO in 3 hours, to give 10 weight percent 3-hydroxypropanal (HPA) intermediate, with some minor hydrogenation to 1,3-propanediol (PDO). This result corresponds to an effective reaction rate of 15 moles of HPA formed per mole of Co catalyst per hr (TOF). Apparent selectivity to acetaldehyde, expressed as the molar ratio of acetaldehyde to the sum of HPA and acetaldehyde, was 27%.

EXAMPLE 2

This comparison example illustrates the hydroformylation of ethylene oxide catalyzed by a phosphine-ligated cobalt carbonyl catalyst, starting with a cobalt(II) salt.

The reactor system of Example 1 was charged with 1.82 grams of "cobalt octoate" (cobalt(II) 2-ethylhexanoate), 0.5 grams of bidentate phosphine (1,2-bis-(9-phosphabicyclononyl)ethane), 0.14 grams of sodium acetate trihydrate, 1.5 grams of toluene (internal standard for reaction), and 147.5 grams of Neodol® 23 solvent. Reactor contents were heated to 90° C. for 1 hour under 1300 psig of 1:1 $H_2$/CO synthesis gas, before injection of about 30 grams of EO. A reaction sample withdrawn after 2 hours indicated formation of 16.4 wt % HPA, at a rate (TOF) of 36 $h^{-1}$, with an apparent selectivity of 15% acetaldehyde.

EXAMPLE 3

This comparison example illustrates the importance of solvent selection in a hydroformylation reaction carried out in the absence of a phosphine ligand for the cobalt catalyst. The reactor system of Example 1 was charged with 0.87 grams dicobaltoctacarbonyl, 0.14 grams sodium acetate trihydrate, 1.5 grams toluene, 1.53 grams 2-ethylhexanoic acid and 146 grams of Neodol® 23. Reactor contents were heated to 125° C. for three hours under 1450 psig 1:1 synthesis gas, before reducing the temperature to 90° C. for injection of 20 grams of ethylene oxide.

Gas uptake virtually ceased after two hours. Only 1 weight percent HPA was formed, at a rate (TOF) of 2.2 h$^{-1}$, and with an apparent selectivity to acetaldehyde of 60%. Infrared spectra of the final solution indicated an absence of cobalt carbonyls, which together with the observation of solid precipitates indicated decomposition and precipitation of cobalt catalyst.

This example shows that, in the absence of phosphine ligand, EO hydroformylation reaction performance is poor for the alcohol solvent system used. Relatively low Ostwald coefficients (volume of gas absorbed at one atmosphere, 298K, per unit volume of liquid) of approximately 0.1 have been reported for carbon monoxide solubility in $C_{11}$–$C_{16}$ alcohol solvents in "Solubility Data Series", R. W. Cargill, ed., Vol. 43, Pergamon Press, NY (1990).

EXAMPLE 4

This experiment illustrates the effect of a suitable hydroformylation solvent. A reaction was conducted with 0.87 grams dicobaltoctacarbonyl, 1.5 grams toluene (internal marker), and 148.5 g methyl-t-butyl ether. After pre-equilibration of the reaction mixture for 1 hour under 1:1 synthesis gas at 80° C., 20 grams EO were added. During the reaction, 3.7 wt % HPA had been formed at approximately 25% conversion at a zero-order rate (TOF) of 4.6 h$^{-1}$.

EXAMPLE 5

This example illustrates the effect of a suitable ethylene oxide hydroformylation promoter. Example 4 was repeated with addition of 0.14 g of sodium acetate trihydrate. At approximately 25% conversion, 4.7 wt % HPA was formed by hydroformylation at 80° C., 1:1 synthesis gas, at a rate (TOF) of 15 h$^{-1}$. This represents a more than 3-fold increase in rate over that observed in the absence of sodium acetate promoter in Example 4.

EXAMPLE 6

The conditions of Example 4 were repeated, except that 2.7 g of deionized water were employed to accelerate the reaction and only 10 g of EO were added to initiate reaction. At approximately 50% conversion, HPA formation was 4.8 wt %, a rate (TOF) of 10 h$^{-1}$, or twice the rate of hydroformylation (4.6 h$^{-1}$) in Example 4 with no added water.

EXAMPLE 7

Example 4 was repeated with 0.077 grams of potassium chloride instead of the sodium acetate. Only 3.7 wt % HPA was formed in 3.5 hours at 80° C. for a rate (TOF) of 4.0 h$^{-1}$. A second run was conducted under otherwise identical conditions, with 0.06 g sodium chloride instead of potassium chloride. At approximately 25% conversion of EO, a zero-order rate of only 4.3 h$^{-1}$ was achieved. These experiments demonstrate the limited effectiveness of neutral salts of strong acids and bases in promoting the hydroformylation reaction.

EXAMPLE 8

The conditions of Example 4 were repeated, except that a mixture of 30% MTBE in tetrahydrofuran was used as the solvent. 4.3 wt % HPA was produced at a rate (TOF) of 8.0 h$^{-1}$, a 70% increase in rate compared with that achieved with less polar MTBE alone as solvent.

EXAMPLE 9

Experiments 9a and 9b demonstrate the increase in rate observed at higher $H_2$/CO ratios and formation of greater than 5 wt % HPA in the absence of phosphine ligand. The reaction in Example 5 (with sodium acetate) was repeated with a 2:1 $H_2$/CO pressure in the reaction, with resupply of 1:1 syngas during reaction to maintain the desired 2:1 syngas ratio and injection of 10 g EO (Example 9a). A zero-order rate (TOF) of 24 h$^{-1}$ was obtained upon formation of 6.2 wt % HPA. This represents a 63% increase in rate over that observed in Example 5. For Example 9b, the above reaction was repeated at $H_2$/CO of 2.3. At approximately 50% conversion, a zero-order rate of 41 h$^{-1}$ was observed (2.7-fold increase relative to Example 5). Ultimately, 7.8 wt % HPA was formed at 90% conversion of EO, at an overall selectivity to HPA and PDO of 84% and an overall rate of 20 h$^{-1}$.

EXAMPLE 10

This experiment illustrates the moderate effectiveness of strong hydroxide bases as hydroformylation reaction promoters. 0.87 g dicobaltoctacarbonyl, 1.5 g toluene (marker), 144.2 g MTBE and 0.5 g of 1N sodium hydroxide were used to hydroformylate 20 g EO at 80° C. and 1:1 CO/$H_2$. At approximately 25% conversion 4.3 wt % HPA was formed at a rate (TOF) of 10.8 h$^{-1}$ or a 60% increase in rate over that observed in the absence of NaOH at a similar water concentration.

The experiment was repeated with the addition of 0.12 g of 30% ammonium hydroxide solution. Only 3.1 wt % HPA was formed in 3.5 hours, for a rate (TOF) of 4.0 h$^{-1}$.

EXAMPLE 11

This comparison experiment illustrates separation of HPA from the cobalt hydroformylation catalyst by distillation. 113.45 g of EO hydroformylation reaction product containing 14.32 g of HPA intermediate were diluted with 50.1 g of tetraethylene glycol dimethylether ("tetraglyme"). The mixture was distilled via a short-path batch still at 10 mm Hg under a slow nitrogen purge at a distillate bottoms temperature ranging from 66° to 108° C. Distillate fractions were collected and were found by gas chromatographic analysis to contain 6.32 g HPA. No HPA was evident in the remaining bottoms sample, which exhibited a significant increase in components heavier than HPA. Total HPA recovery was thus 44% with the remainder degraded to heavy ends.

This experiment demonstrates the problems inherent in thermal separation of highly-reactive HPA intermediate from the reaction mixture. More than half the HPA intermediate was degraded during the separation.

EXAMPLE 12

This invention experiment demonstrates separation and concentration of HPA by water extraction. 1507.6 g of EO hydroformylation reaction product (MTBE solvent with sodium acetate promoter at 0.2 Na/Co) containing 6.0 wt % HPA intermediate were water extracted at 25° C. under 100 psig nitrogen in a stirred reactor with 298 g of deionized water, giving 400.5 g of a lower layer containing 20.8 wt % HPA intermediate (3.5-fold concentration). Overall HPA material balance from gas chromatographic analysis of feed, upper phase and lower phase indicated 106% recovery of HPA, or complete recovery within g.c. experimental error.

The upper layer following water extraction contained 0.14 wt % cobalt, or 65% of the initially-charged catalyst.

This experiment demonstrates the catalyst and product recovery advantages of the invention PDO preparation method. Separation of HPA from the reaction mixture was very efficient and selective. The use of water and low temperatures avoided the degradation of HPA shown in Example 11. The method also allows concentration of HPA for more efficient hydrogenation and final recovery. In addition, a significant fraction (65%) of the cobalt catalyst was readily separated from aqueous HPA product, making efficient recycle of catalyst with reaction solvent possible.

EXAMPLE 13

This example illustrates hydrogenation of aqueous HPA obtained from water extraction of the product of ethylene oxide hydroformylation. 333.4 g of extract containing 20 wt % HPA were added to a 500 ml autoclave reactor containing 5.07 g of a powdered supported nickel hydrogenation catalyst (Calsicat E 475SR, 50% Ni). The reactor was charged with 1000 psig $H_2$ and heated to 60° C. for 3 hours. At this time, gas chromatographic analysis indicated 99% conversion of HPA, at 93% selectivity to PDO (moles PDO formed divided by moles HPA consumed) and 3% selectivity to propanol. The reaction temperature was increased to 90° C. for one hour, after which an HPA conversion in excess of 99% was indicated, at an apparent selectivity of 99% PDO and 3.5% propanol. Heating was continued for one additional hour at 110° C. to give an apparent selectivity of 110% PDO and 4.5% propanol. (Apparent selectivities in excess of 100% and continued formation of PDO after consumption of HPA can be explained by reversion of heavy ends formed during hydroformylation or early hydrogenation.)

EXAMPLE 14

In order to examine the role of the promoter, a series of reactions was carried out in a small-scale reactor fitted with optics for in situ infrared analysis. In the first reaction, 80 mg (0.234 millimoles) of recrystallized (from $CH_2Cl_2$) dicobalt octacarbonyl were added to 17 ml of dried and distilled methyl-t-butyl ether in the 30 ml reactor bottom fitted with a ZnS (45°) infrared crystal. The top was closed onto the unit and the reactor assembly was removed from the dry box. The inert atmosphere was replaced with carbon monoxide by alternately pressurizing the reactor to 200 psig with CO and then depressurizing the vessel to atmospheric pressure for a total of 3 cycles. The unit was finally pressurized to 200 psig with CO. The unit was then heated to 80° C. and the pressure in the reactor was adjusted to 375 psig with pure CO. 1.2 g (27 millimoles) of ethylene oxide were added to the reactor with hydrogen gas pressure, bringing the total pressure inside the unit to 1600 psig to produce a 3:1; $H_2$:CO gas cap. Infrared spectra were recorded at 3 minute intervals to monitor the progress of the reaction. The pressure in the unit dropped due to gas consumption and syngas (1:1) was added as required to maintain the total pressure in the reactor between approximately 1550 and 1500 psig. A reactor profile of pressure and temperature data was measured digitally via transducer and thermocouple.

The second reaction was carried out in a like manner except that 16 mg (0.096 millimoles) of sodium octoate was also added to the reaction mixture. The rate of HPA formation was calculated from syngas consumption and checked against the appearance of aldehyde at 1724 $cm^{-1}$ and the disappearance of the ethylene oxide band in the infrared spectrum at 870 $cm^{-1}$. The TOF of the reaction in the absence of a promoter was 15 $h^{-1}$ and in the presence of sodium octoate the TOF was 41 $h^{-1}$. At the beginning of the reaction, the infrared spectrum of the catalyst region (2300–2000 $cm^{-1}$) displayed patterns characteristic of dicobalt octacarbonyl. The reaction run in the absence of a promoter showed no change in this region of the infrared over the course of the reaction. In contrast, the reaction run with the promoter changes rapidly producing a pattern characteristic of the cobalt acyl complex in addition to the patterns from dicobalt octacarbonyl. This indicates that the promoter changes the rate determining step in the reaction cycle, resulting in a faster overall reaction rate.

EXAMPLE 15

An experiment was performed to test the effectiveness of a lipophilic phosphine oxide promoter in accelerating the hydroformylation reaction. As a control experiment, a 300-ml stirred batch reactor was charged under nitrogen with 0.87 g dicobaltoctacarbonyl, 1.5 g toluene (marker). 2 g deionized water and 146 g methyl-t-butyl ether (MTBE). The nitrogen atmosphere was flushed with $H_2$, and the reactor was filled to 600 psig $H_2$ and then to 1200 psig with 1:1 $CO/H_2$. Reactor contents were heated to 80° C. for one hour, and 10 g of ethylene oxide were then injected, with simultaneous increase in reactor pressure to 1500 psig via addition of 1:1 $CO/H_2$. Reactor contents were sampled and analyzed via capillary g.c. (with flame ionization detector) at approximately 40% and nearly 100% conversion of EO, which occurred within two hours. At approximately 40% conversion, 3.3 wt % HPA had been formed at a rate of 18 $h^{-1}$.

The experiment was repeated with addition of 0.4 g of triphenylphosphine oxide as promoter, for a ratio of 0.26 moles promoter per mole of cobalt. At approximately 50% conversion, 4.3 wt % HPA had been formed at a rate of 39 $h^{-1}$, or more than a two-fold rate increase over that observed in the absence of promoter. The reaction was terminated at 95% conversion of ethylene oxide with formation of 8.6 wt % HPA.

EXAMPLE 16

A series of experiments was performed to test the effectiveness of lipophilic amine promoters in accelerating the hydroformylation reaction. As a control experiment, a 300-ml stirred batch reactor was charged under nitrogen with 0.87 g dicobaltoctacarbonyl, 1.5 g toluene (marker), 1.5 g undecanol (second marker), and 147 g methyl-t-butyl ether (MTBE). The nitrogen atmosphere was flushed with $H_2$ before the reactor was filled to 1200 psi with 1:1 $CO/H_2$. Reactor contents were heated to 80° C. for 45 minutes, before injection of 20 g ethylene oxide, with simultaneous increase in reactor pressure to 1500 psi by addition of 1:1 $CO/H_2$. Reactor contents were sampled and analyzed via capillary g.c. (with flame ionization detector) at approximately 1.5 hours and 3.3 hours. At approximately 1.5 hours, 1.8 wt % HPA had been formed at a zero-order rate of 4.9 g moles-HPA per gmole-cobalt per hour (1/h).

The above procedure was repeated, with addition of 0.15 g of pyridine, at a molar ratio N/Co of 0.37. After 68 minutes, 4.13 wt % HPA had been formed at a rate of 14.5 gmoles/gmole-Co/h, or a 2.9-fold increase over the rate obtained in the absence of promoter.

The conditions of the control experiment were repeated at an $H_2$/CO ratio of 2.3 with addition of 0.5 g of dimethyldodecylamine and injection of 12 g of ethylene oxide. Sampling after 45 minutes of reaction indicated formation of 5.7 wt % HPA, for a rate of 31 gmole/gmole-Co/h. This corresponds to a 1.5-fold rate increase over that observed under the same conditions in the absence of promoter. The reaction was continued until formation of 10 wt % HPA at virtually complete conversion of ethylene oxide. Following the reaction, the mixture was cooled to 25° C. and extracted with 30 g deionized water under 300 psi CO. The mixture was then transferred to a separation vessel under 100 psi CO. Separation yielded 30.75 g of a lower aqueous layer containing 24.0 wt % HPA, and an upper organic solvent layer containing 1.0 wt % HPA. Colorimetric analysis of upper and lower layers indicated 94% of the cobalt catalyst to reside in the upper solvent layer, demonstrating separation of a majority of cobalt catalyst from a majority of HPA product.

EXAMPLE 17

An experiment was performed to assess the effectiveness of a lipophilic dihydroxyarene as a promoter for the hydroformylation reaction. The control experiment of Example 15 was repeated with addition of 0.14 g of hydroquinone as promoter, for a ratio of 0.25 moles promoter per mole of cobalt. At approximately 50% conversion, 4.7 wt % HPA had been formed at a rate of 25.9 h$^{-1}$, or a 44% rate increase over that observed in the absence of promoter. The reaction was terminated at 98% conversion of ethylene oxide, with formation of 9.4 wt % HPA.

Following the reaction, the mixture was cooled to room temperature. 31.6 g of deionized water were added for extraction of product under 200 psig synthesis gas. After 30 minutes, mixing was terminated and 38.32 g of an aqueous product layer containing 18 wt % HPA was isolated. The aqueous layer contained 115 ppm cobalt, or only 4% of the total charged. The upper organic layer (99.8 g) was analyzed to contain 0.19 wt % cobalt, or about 96% of the cobalt catalyst.

We claim:

1. A process for preparing 1,3-propanediol comprising the steps of:
   (a) contacting, at a temperature within the range of about 50° to about 100° C. and a pressure within the range of about 500 to about 5000 psig, ethylene oxide with carbon monoxide and hydrogen in an essentially non-water miscible solvent in the presence of an effective amount of a non-phosphine-ligated cobalt catalyst and an effective amount of a catalyst promoter under reaction conditions effective to produce an intermediate product mixture comprising less than 15 wt % 3-hydroxypropanal;
   (b) adding an aqueous liquid to said intermediate product mixture and extracting into said aqueous liquid a major portion of the 3-hydroxypropanal at a temperature less than about 100° so as to provide an aqueous phase comprising 3-hydroxypropanal in greater concentration than the concentration of 3-hydroxypropanal in the intermediate product mixture, and an organic phase comprising at least a portion of the cobalt catalyst or a cobalt-containing derivative thereof;
   (c) separating the aqueous phase from the organic phase;
   (d) contacting the aqueous phase comprising 3-hydroxypropanal with hydrogen in the presence of a hydrogenation catalyst at a pressure of at least about 100 psig and a temperature during at least a portion of the hydrogenation step of at least about 40° C. to provide a hydrogenation product mixture comprising 1,3-propanediol; and
   (e) recovering 1,3-propanediol from the hydrogenation product mixture.

2. The process of claim 1 in which the solvent of step (a) comprises an ether.

3. The process of claim 1 in which the 3-hydroxypropanal in the intermediate product mixture is produced at a level within the range of about 5 to about 10 wt %.

4. The process of claim 3 in which step (a) is carried out at a temperature within the range of about 60° to about 90° C.

5. The process of claim 4 in which step (a) is carried out at a pressure within the range of about 1000 to about 3500 psig.

6. The process of claim 1 which further comprises carrying out step (b) under carbon monoxide.

7. The process of claim 5 in which the solvent of step (a) has an Ostwald coefficient for carbon monoxide solubility greater than 0.15 v/v.

8. The process of claim 5 in which the solvent of step (a) comprises methyl-t-butyl ether.

9. The process of claim 1 in which the reaction mixture comprises 0 to about 2.5 wt % water.

10. The process of claim 1 in which the solvent of step (a) has a solubility in water at 25° C. of less than about 10%.

11. The product of claim 1 in which the catalyst promoter comprises an alkali, alkaline earth or rare earth metal salt of a carboxylic acid.

12. The process of claim 11 in which the promoter is sodium acetate.

13. The process of claim 11 in which the promoter is present in an amount within the range of about 0.01 to about 0.6 moles per mole of cobalt.

14. The process of claim 1 in which the carbon monoxide and hydrogen of step (a) are present in an $H_2/CO$ ratio within the range of about 1.5:1 to about 5:1.

15. The process of claim 1 in which step (a) is carried out at a rate (TOF) greater than about 30 h$^{-1}$.

16. A process for preparing 1,3-propanediol comprising the steps of:
   (a) reacting ethylene oxide, carbon monoxide and hydrogen in a solvent comprising methyl-t-butyl ether at a temperature within the range of about 75° to about 85° C. in the presence of a catalytic amount of a non-phosphine-ligated cobalt carbonyl and a promoting amount of sodium acetate, under hydroformylation conditions effective to produce an intermediate product mixture comprising 3-hydroxypropanal in a concentration within the range of about 0.5 to about 1 molar;
   (b) adding, at a temperature within the range of about 25° to about 55° C., an aqueous liquid to said intermediate product mixture in an amount within the range of about 5 to about 20 weight percent based on the weight of the intermediate product mixture, and permitting the water-containing intermediate product mixture to resolve into an aqueous phase comprising 3-hydroxypropanal in a concentration of at least about 20 wt %, and an organic phase comprising a major portion of the cobalt carbonyl;
   (c) separating the aqueous phase from the organic phase;
   (d) contacting the aqueous phase comprising 3-hydroxypropanal with hydrogen in the presence of a hydrogenation catalyst at a pressure of at least about 100 psig and a temperature of at least about 40° C. to provide a hydrogenation product mixture comprising 1,3-propanediol; and
   (e) recovering 1,3-propanediol from the hydrogenation product mixture.

17. The process of claim 16 which further comprises removing cobalt catalyst from the aqueous phase of step (c).

18. The process of claim 16 in which the aqueous phase of step (b) comprises 3-hydroxypropanal in a concentration greater than about 35 wt %.

* * * * *